United States Patent [19]

Furuto et al.

[11] 4,041,376

[45] Aug. 9, 1977

[54] DETECTOR FOR DETECTING THE STATE OF ELECTRICALLY NON-CONDUCTIVE OR SUBSTANTIALLY ELECTRICALLY NON CONDUCTIVE FLUID

[75] Inventors: Yoshio Furuto, Naka; Masaaki Ban, Tokyo, both of Japan

[73] Assignee: The Furukawa Electric Co., Ltd., Tokyo, Japan

[21] Appl. No.: 455,296

[22] Filed: Mar. 27, 1974

[30] Foreign Application Priority Data

Nov. 6, 1973  Japan .......................... 48-124725

[51] Int. Cl.$^2$ .................... G01N 27/00; G01F 1/00
[52] U.S. Cl. .................... 324/33; 250/384; 73/194 F
[58] Field of Search ............... 324/33; 250/356, 364, 250/379, 384; 73/194 F

[56] References Cited

U.S. PATENT DOCUMENTS

| | | | |
|---|---|---|---|
| 2,861,452 | 11/1958 | Morgan | 73/194 F |
| 3,662,177 | 5/1972 | Sasaki et al. | 250/379 |
| 3,706,938 | 12/1972 | Petriw | 324/33 |

FOREIGN PATENT DOCUMENTS

| | | | |
|---|---|---|---|
| 1,933,938 | 2/1970 | Germany | 324/33 |
| 1,901,189 | 7/1970 | Germany | 324/33 |
| 810,062 | 3/1959 | United Kingdom | 250/384 |

*Primary Examiner*—John K. Corbin
*Assistant Examiner*—Rolf Hille
*Attorney, Agent, or Firm*—Woodling, Krost, Granger & Rust

[57] ABSTRACT

This invention relates to a detector for detecting the state of electrically non-conductive or substantially electrically non-conductive fluid, such as its flowing velocity, direction, composition or pressure, comprising a transducer to generate an electric signal responsive to said state of said fluid, said transducer having at least one ionizing area exposed to said fluid and said electric signal appearing as variation in conductance across said ionizing area, an amplifier to amplify said electric signal from said transducer, having a high input impedance and a low output impedance, and means to shield said transducer and said amplifier.

9 Claims, 13 Drawing Figures

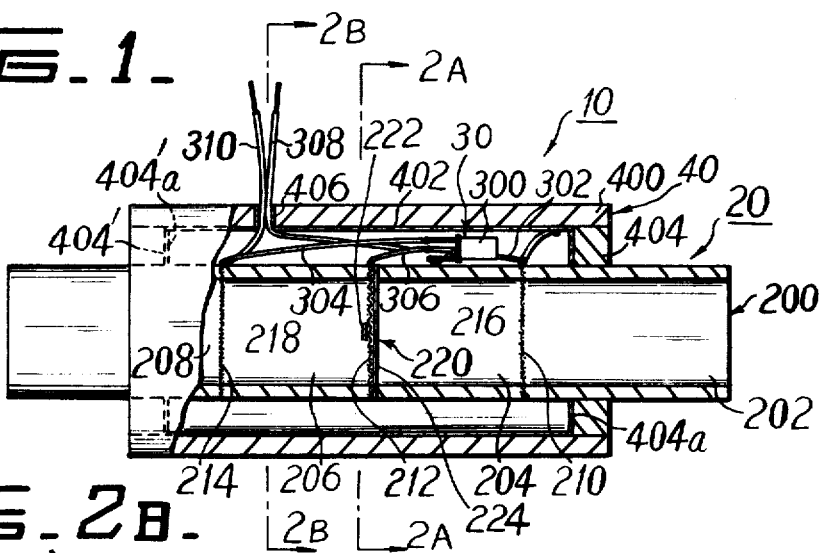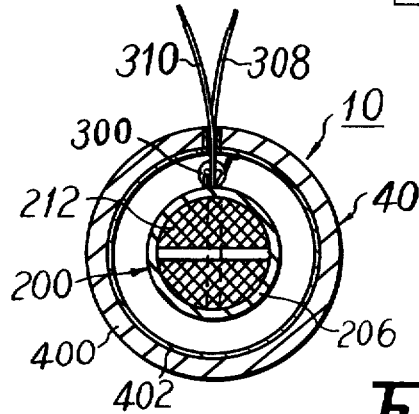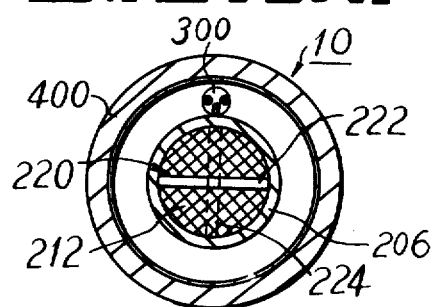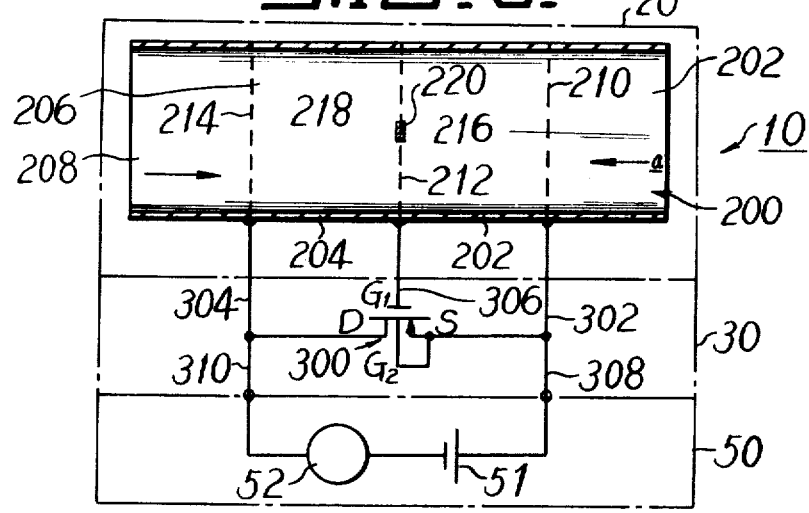

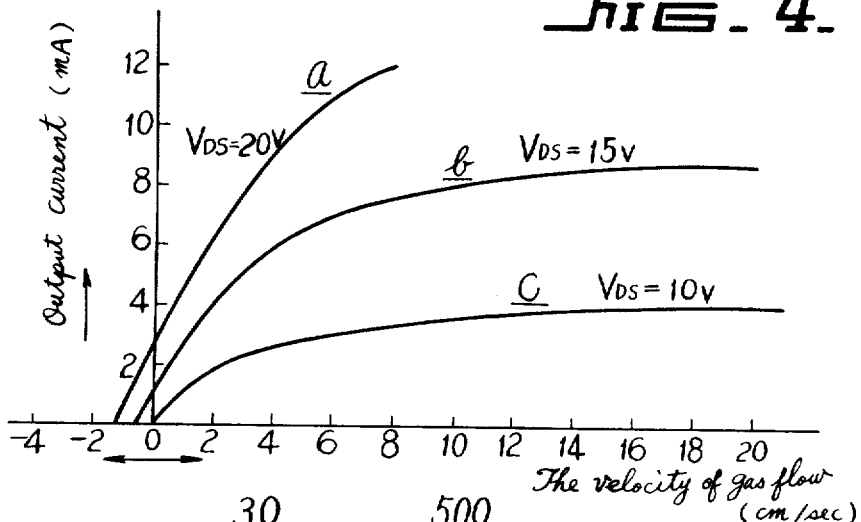
FIG_4.
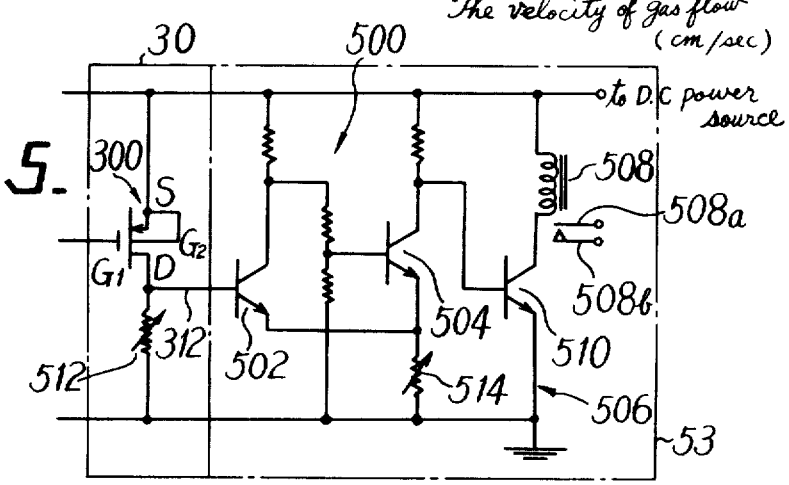
FIG_5.
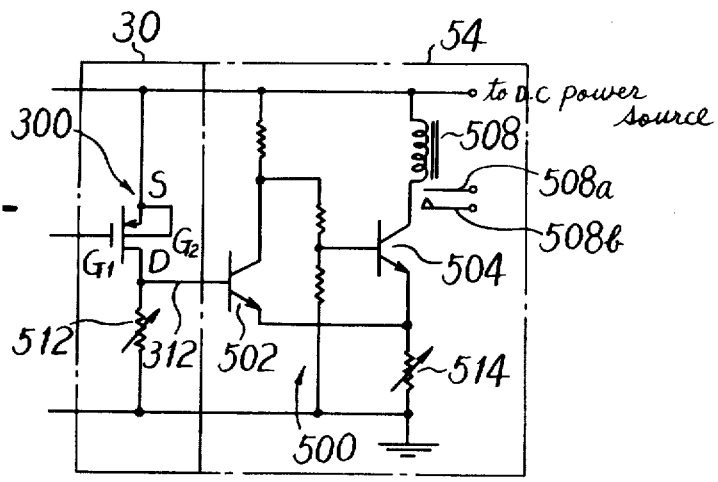
FIG_6.

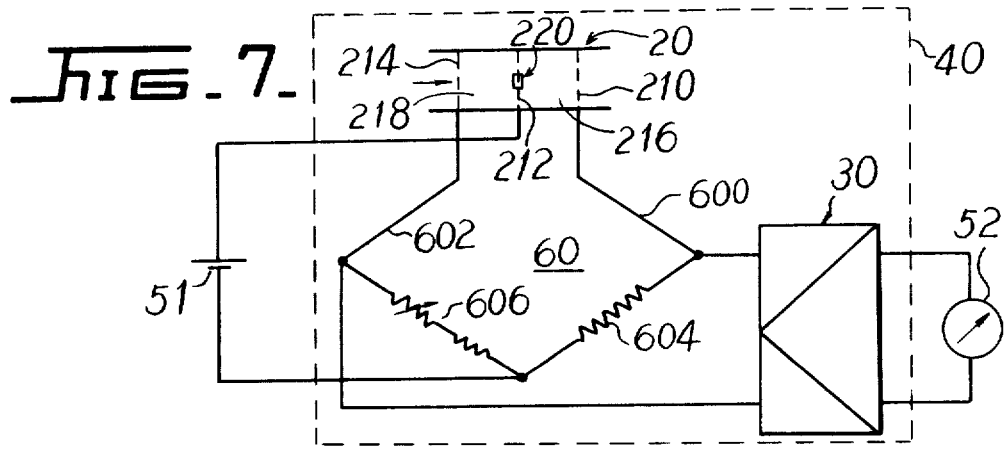
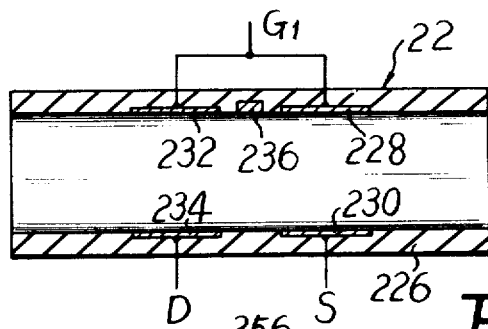
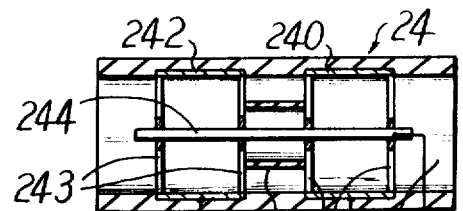
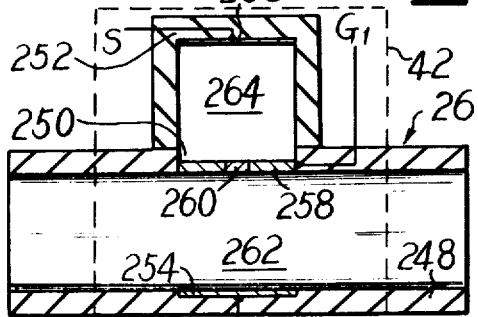
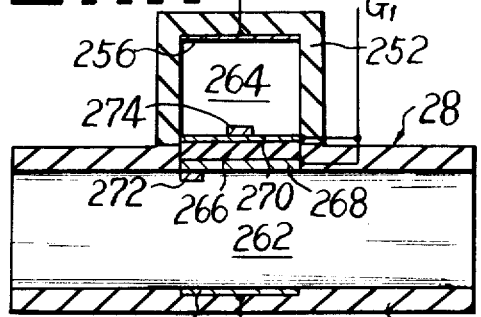
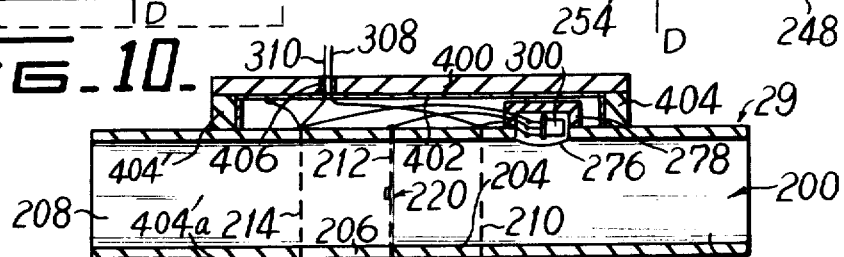

DETECTOR FOR DETECTING THE STATE OF ELECTRICALLY NON-CONDUCTIVE OR SUBSTANTIALLY ELECTRICALLY NON CONDUCTIVE FLUID

BACKGROUND OF THE INVENTION

The arts in which for detection of the state of electrically non-conductive fluid radiation from a radiation source ionizes the fluid and the concentration of the ionized fluid is electrically detected are well known. The prior arts are disclosed in U.S. Pat. Nos. 2,611,268, 2,627,543, 2,861,452, 3,683,178 and 3,706,938, for example. Briefly, the prior arts employ variation in ion distribution or electrical conductance across electrodes between which runs the fluid ionized by radiation from a radiation source, said variation produced responsive to the presence, direction, velocity, etc. of the fluid flow. Some of the prior arts include electrode means oppositely disposed laterally of the central plane of the radiation source, so that electrode means may differentially detect the ion distributions or conductances upstream and downstream of the fluid flow. One of the common disadvantages of the prior arts is that the electric signal from electrode means tends to be affected by external induction. More particularly, since a transducer comprising the radiation source and electrode means has a high impedance, an amplifier connected to the transducer is required to have a high input impedance for matching. Due to high input impedance of the amplifier, leads between the transducer and the amplifier tend to have external noise induced. Such external noise causes the output signal from the amplifier to become unstable and also the state of faint fluid flow to be unable to be positively detected. Specially, when the fluid to be measured is liquid radiation passing through liquid has a greater attenuation and also the generated ions have shorter life time, resulting in lower output from the transducer. Thus, the effect by external noise must be avoided. Moreover, due to the floating capacity of the leads between the transducer and the amplifier, the state of the fluid is detectable only with a lower response.

Another disadvantage of the prior arts is that they cannot detect any of the volumetric flow rate, composition and pressure of the fluid. Furthermore, the amplifier is required to be stably operated even when it is placed in varied ambient temperatures.

OBJECTS OF THE INVENTION

Accordingly, it is a principal object of the present invention to provide a detector for detecting the state of generally electrically non-conductive fluid wherein an output signal from a transducer can be picked up without any obstruction by external induction.

It is another object of the present invention to provide a detector of the above type wherein the state of the fluid can be detected with a higher sensitivity and with a higher signal-to-noise ratio.

Further object of the present invention is to provide a detector of the above type wherein the state of the fluid can be detected with a higher response.

Another object of the present invention is to provide a detector of the above type wherein the state of the fluid can be detected without being affected by ambient temperature.

SUMMARY OF THE INVENTION

According to one aspect of the present invention, there is provided a detector for detecting the state of generally electrically non-conductive fluid, comprising a transducer to generate an electric signal responsive to the state of said fluid, said transducer including a conduit into which said fluid is introduced, a radiation source to ionize said fluid in said conduit and at least one ionizing area having a pair of spaced electrodes exposed to said ionized fluid, said ionizing area defined by said conduit and said electrodes; means to shield said transducer; and an amplifier having a high input impedance and a low output impedance disposed within said shield means and connected to said electrodes.

According to another aspect of the present invention, there is provided a detector for detecting the state of generally electrically non-conductive fluid, comprising a transducer to generate an electric signal responsive to the state of said fluid, said transducer including a conduit into which said fluid is introduced, a radiation source to ionize said fluid in said conduit, an ionizing area having a pair of spaced electrodes exposed to said ionized fluid, said ionizing area defined by said conduit and said electrodes, a closed ionizing chamber containing generally electrically non-conductive reference fluid and having a pair of spaced electrodes exposed to said reference fluid in said chamber and a second radiation source to ionize said reference fluid in said chamber; means to shield said transducer; and an amplifier having a high input impedance and a low output impedance disposed within said shield means and connected to said electrodes for both said ionizing area and said closed chamber of said transducer.

BRIEF DESCRIPTION OF THE DRAWINGS

The above and other objects and features of the present invention will become apparent from the description of the preferred embodiments taken with reference to the accompanying drawings;

FIG. 1 is a front view of one preferred embodiment of a detector for detecting the state of fluid according to the present invention with portions broken away;

FIG. 2A is a cross sectional view of the detector of FIG. 1 taken along the line 2A—2A of FIG. 1;

FIG. 2B is a cross sectional view of the detector taken along the line 2B—2B of FIG. 1;

FIG. 3 is a schematic diagram of the detector of FIG. 1 and an external detecting circuit associated with the former;

FIG. 4 shows a graph illustrating a detecting current through an external circuit against the velocity of fluid through the detector of FIG. 1;

FIG. 5 is a schematic diagram of alternative example of the external detecting circuit associated with the detector as shown in FIG. 1;

FIG. 6 is a schematic diagram of another example of the external detecting circuit associated with the detector as shown in FIG. 1;

FIG. 7 is a schematic diagram of the detector of FIG. 1 and another external detecting circuit in combination;

FIG. 8 is a vertical sectional view of another transducer employed in the detector of the present invention;

FIGS. 9 to 11 are vertical sectional views of other transducers employed in the present invention; and FIG. 12 is a vertical sectional view of another embodiment of the detector according to the present invention.

DETAILED DESCRIPTION OF PREFERRED EMBODIMENTS

Referring to FIG. 1 of the accompanying drawings, a detector for detecting the state of fluid in accordance with the present invention is generally indicated by reference number 10, which comprises a transducer 20 electronically responding to the flow of electrically non-conductive or substantially electrically non-conductive fluid through the transducer.

The transducer 20 may include a conduit 200 comprising four pipe blocks 202 to 208 of polyvinyl chloride, the adjacent pipe blocks of which may together adhere to each other at the end faces thereof. A net-like or grid electrode 210 of copper is held between the opposing end faces of the pipe blocks 202 and 204 and secured thereto by adhesion of the blocks. Similarly, net-like or grid electrodes 212 and 214 of copper are held between and secured to the opposing end faces of the pipe blocks 204 and 206, respectively. Because of the same length of the pipe blocks 204 and 206, the electrodes 210 and 214 are disposed symmetrically of the central electrode 212, as shown in FIG. 1.

An ionizing area 216 is defined by the pipe block 204 and the electrodes 210 and 212 and similarly an ionizing area 218 is defined by the pipe block 206 and the electrodes 212 and 214. The central electrode 212 may carry a radiation source 220 which may comprise two americium tapes clad with either gold alloy or aluminium. As shown in FIGS. 2A and 2B, the americium tapes 222 and 224 may be made to adhere onto the opposite faces of the electrode 212 in a diagonal relation to the electrode and in an orthogonal relation of one of the tapes to the other and may be preferably held and secured at the opposite ends between the pipe blocks 204 and 206 together with the electrode 212. Of course, it will be understood that any of other radiation sources may be employed which radiates abundant α-rays having long half life and high ionization energy. The other radiation sources may include isotopes such as radium and cesium, and an alloy of any of the isotopes and metal, for example.

The pipe blocks 202 and 208 are connected through fittings (not shown) to a passage through which the non-conductive fluid flows. The non-conductive fluid, which can be detected by the transducer 20, includes gases such as $H_2$, $N_2$, $O_2$, Ar, Ne, $CO_2$, $CH_4$, $C_2H_6$, $SF_6$ and air, for example and liquids such as liquefied gases including liquefied nitrogen, liquefied helium, LNG, etc., benzol, toluene, volatile oil, etc.. It will be noted that the fluid which can be detected by the transducer also includes substantially electrically non-conductive fluid such as water. The detector which is adapted to detect the state of water will be later described in connection with FIG. 7. The fluid, which passes through the transducer is ionized by radiation from the source 220 in the transducer 20. The arrangement of the electrodes in the transducer 20 is substantially similar to that of the above-mentioned U.S. Pat. No. 3,706,938 except that the electrodes are disposed within the conduit 200. Although the transducer 20 is conventional, the operation of the transducer will be briefly described as follows; assuming that the fluid is stationary in the conduit 200, the ions within the conduit are symmetrically distributed in both of the ionizing areas 216 and 218 relative to the central electrode 212. Accordingly, when voltage is applied across the electrodes 210 and 214, then the electrode 212 has one half potential of the applied voltage across the electrodes 210 and 214. Assuming that the fluid flows within the conduit 200, the ionized fluid is forced downstream along its direction, with the result that the ion distribution is so varied that the concentration of the ions is less upstream and more downstream. Therefore, upon application of voltage across the electrodes 210 and 214 potential difference between the central and downstream electrodes would be less than that between the central and upstream electrodes. Variation in the potential differences depends upon the direction, velocity and volumetric rate of the fluid flow. Thus, it will be noted that the transducer 20 has variable conductances across the respective ionizing areas responsive to variation in the state of fluid flow.

The detector 10 of the present invention is also provided with an amplifier 30 which has high input impedance for matching high internal impedance of the transducer 20. In the illustrated embodiment, the amplifier 30 may comprise an enhancement type metal oxide field effect transistor (MOS-FET) 300, but may alternatively comprise a junction type FET. Of course, otherwise it may comprise any other amplifier having a high input impedance. The FET, which is known to have a channel produced by electrostatic induction upon application of gate voltage, can be preferably operated in a stable manner. Also, the FET preferably has low output impedance to provide the impedance conversion thereto, which will be described hereinafter. As shown in FIG. 3, the electrodes 210 and 214 of the transducer 20 may be connected through respective leads 302 and 304 to the source S and drain D of the FET 300, respectively and the central electrode 212 of the transducer 20 may be connected through a lead 306 to the gate $G_1$ of the FET 300. Referring again to FIG. 1, the FET 300 is shown to be disposed adjacent to the periphery of the conduit 200 of the transistor 20. The connection of the leads 302 to 306 with the respective electrodes is effected by soldering the leads to the exposed edges of the respective electrodes.

The detector 10 of the present invention also comprises means 40 to shield both the transducer 20 and the amplifier 30. In the illustrated embodiment, the shield means 40 may comprise a cylindrical casing 400 of polyvinyl chloride lined on its inner surface with an electrically conductive shielding layer 402 of metal such as aluminium and spacedly disposed around the circuit 200 of the transducer 20. The casing 400 is provided at both ends with supporting ring members 404 and 404' of polyvinyl chloride which are bonded at the outer periphery with the casing 400 and at the inner surface with the pipe blocks 202 and 208, respectively by any suitable means. The ring members 404 and 404' are preferably lined with shielding metal layers 404a and 404'a. Alternatively, the shield metal layers may comprise any other metal than aluminium and may also be in the form of net, plating layer or the like. Otherwise, the shield layer may be omitted by use of the metal casing 400 and the metal ring members 404 and 404'. The leads 302 to 306 are also disposed together with the FET 300 within the casing 400. Leads 308 and 310, which are connected to the source S and drain D of the FET 300, extend out through a bush 406 in the casing 400 and are adapted to be connected to an external detecting circuit 50 which will be described in detail hereinafter.

The shield means 40 surrounding the transducer 20 and the amplifier 30 as shown in FIGS. 1 and 2 is one of the important features of the present invention. More specifically, since the FET 300 serves to convert high 300 and the ground as in FIG. 5. With the actuating circuit, when the fluid is flowing through the transducer 20 of FIG. 1 in the direction indicated by an arrow, the transistor 504 does not conduct so that the relay 508 is not energized. If the fluid stops flowing, the transistor 504 is so conductive that the relay 508 is energized to close the contactors 508a and 508b. The closed relay contactors 508a and 508b operates a warning circuit associated with the contactors for warning that the fluid stops to flow. The warning circuit operated by the actuating circuit 54 is adapted to indicate whether cooling agent within a cooling system of an electric equipment is circulated or not.

Of course, it should be understood that the output from the detector 20 of the present invention may be employed to control the fluid flow.

Referring now to FIG. 7, there is illustrated a modification of the detector 10 of the present invention wherein the amplifier 30 further includes a bridge connection 60 arranged between the transducer 20 and the amplifier 30 and associated with the amplifier 30. The transducer 20 and the amplifier 30 may be similar to those shown in FIG. 3. The bridge connection 60 has two arms 600 and 602 connected to the electrodes 210 and 214 of the transducer 20, respectively and two other arms 604 and 606 comprising resistances, respectively one of which may be preferably variable, as shown in FIG. 7. The DC power source 51 is connected at the positive polarity to the electrode 212 of the transducer 20 and at the negative polarity to the point between the arms 604 and 606. The amplifier 30 is connected at both ends thereof to the points between the arms 600 and 604 and between the arms 602 and 606, respectively. Shield means 40, similar to that of FIG. 1 surrounds all of the transducer 20, the amplifier 30 and the bridge connection 60 in a similar manner. The detector 10 of FIG. 7 is adapted to detect the state of fluid such as water which is substantially non-conductive, but which tends to be electrolyzed even by relatively lower voltage applied. Provided that water is flowing through the transducer 20 in a direction indicated by an arrow of FIG. 7, water ionized by the radiation source 220 is so displaced that the ionizing area 218 has higher internal resistance than when water is stationary, while the ionizing area 216 has lower internal resistance. Of course, it will be noted that the power source 51 is so set that it has a lower voltage than 1.225 volts at which water begins to be electrolyzed. The variable resistance 606 serves to adjustably determine the value so that the output from the bridge connection 60 is zero when water is stationary within the transducer 20. Therefore, when the transducer 20 has an electrical signal produced by lower and higher internal resistances of the ionizing areas 218 and 216, the bridge connection 60 has a positive output signal generated therefrom. The positive signal from the bridge connection is then applied to the amplifier 30 which amplifies and applies it to the external detecting circuit shown to be in the form of the ampere meter 52. Thus, the meter 52 indicates the velocity of water flow through the transducer 20. In measurement of water flow, it has been ascertained that when water flows at the velocity of approximately 10 cm/sec. the detector 20 of FIG. 7 has a gain twice as high as that when water flow is stationary.

FIGS. 8 through 11 show other embodiments of the transducer adapted to be used in the detector of the present invention. A transducer 22 of FIG. 8 comprises a conduit 226 of insulating material having a rectangular cross section. A first pair of electrodes 228 and 230 of copper plate are oppositely mounted on the inner surface of the conduit 226 at the top and bottom thereof and similarly a second pair of electrodes 232 and 234 of copper plate are oppositely mounted on the inner surface of the conduit 226 in a spaced relationship from the first pair of electrodes in the axial direction of the conduit. A radiation source 236, which may be in the suitable form, is mounted on the top of the inner surface of the conduit just intermediate between the electrodes 228 and 232. It should be noted that the two pairs of electrodes 228, 230 and 232, 234 together with the radiation source 236 are flush with the inner surface of the conduit 226. These components can be readily mounted by inserting them into the conduit 226 when moulded. With this arrangement, there is preferably no obstacle which disturbs the flow of the fluid through the transducer 22. Thus, it is adapted to precisely detect faint flow of the fluid therethrough. Furthermore, it is also adapted to detect the state of liquid having a higher density than gas because the dense fluid is never disturbed when flowing through the transducer 22. It will be understood that the electrodes 228 and 230 may be connected to one of the gates $G_1$ of the FET 300 of FIG. 1 and the electrodes 230 and 234 to the drain D and source S of the FET 300, for example. In FIG. 8, the amplifier and the shield means have been omitted for the purpose of simplification of illustration.

A transducer 24 of FIG. 9 comprises a hollow cylindrical conduit 238 of insulating material on the inner surface of which two hollow cylindrical copper electrodes 240 and 242 are mounted in a spaced relationship with each other in the axial direction of the conduit 238. As shown in FIG. 9, the cylindrical electrodes 240 and 242 are embedded in the conduit 238 so that the inner surfaces of the electrodes are flush with the inner surface of the conduit 238, in the similar manner as described in connection with FIG. 8. A central electrode 244 of copper bar is coaxially disposed relative to the cylindrical electrodes 240 and 242 and mounted within the conduit 238 by extending the electrode 244 through central eyes of insulating frames 241 and 243 comprising a plurality of radial arms which at the outer edges are in turn mounted on the cylindrical electrodes 240 and 242 at both ends thereof. A radiation source 246 may be in the form of ring which is coaxially disposed just midway between the cylindrical electrodes 240 and 242 and securely held between the opposite frames 241 and 243 on the cylindrical electrodes 240 and 242. The electrodes 240 and 242 may be connected to the drain D and the source S of the FET 300 of FIG. 1 and the electrode 244 to one of the gates $G_1$ of the FET 300, just as described in connection with FIG. 8. In FIG. 9, the amplifier and the shield means have been also omitted as described in connection with FIG. 8.

A transducer 26 of FIG. 10 is adapted to detect the state of the fluid flow and/or the state of the stationary fluid such as the composition, the pressure and the like. The transducer 26 comprises a conduit 248 of insulating material having a rectangular cross section with a middle portion opened at a position indicated by numeral 250. A casing 252 of insulating material is mounted on the conduit 248 at the opening 250 so that it is closed by the casing 252. A copper plate electrode 254 may be mounted on the conduit 248 at the inner bottom surface opposite from the opening 250 in the conduit in a similar manner as described in connection with the electrodes 228 to 234 of FIG. 8. On the inner top surface of the input impedance into low output impedance, the low impedance output is obtained from the leads 308 and 310. Therefore, the output system of the FET 300 is scarcely affected by any external induction noise so that the FET 300 has highly stable signal output therefrom. This means that the external detecting circuit of high sensitivity can have a high signal-to-noise ratio (S/N ratio). Furthermore, it will be noted that the state of a fluid such as liquid which is difficult to be ionized can be effectively measured.

As seen from FIG. 1, because of the FET 300 disposed adjacent to the electrodes of the transducer 20, the leads 302 to 306 may be shorter than when the FET is not adjacent to the electrodes. This improves the responsiveness of the system because of less floating capacity of the leads.

As shown in FIG. 3, the leads 308 and 310 may be associated with the external detecting circuit 50 which is shown to comprise a DC power source 51 and an ampere meter 52. The DC power source 51 is connected at the positive polarity to the source S of the FET 300 through the lead 308 and at the negative polarity to one end of the ampere meter 52, the other end of which is connected to the drain D of the FET through the lead 310. It will be understood that the current through the ampere meter 52, that is the output current from the FET, depends upon the state of the fluid such as the velocity, direction, or volumetric rate of its flow.

FIG. 4 shows a graph wherein the output current to be measured by the ampere meter 52 is plotted against the velocity of $N_2$ gases flowing through the detector 10 as shown in FIG. 1. In this measurement, the conduit 200 was employed which had the cross sectional area of 2.0 cm² and the net-like electrodes were employed which had the roughness of 150 meshes. The distance between the adjacent electrodes was 50 mm. When the applied voltage $V_{DS}$ across the drain D and source S of the FET was 20V, the curve $a$ was obtained. As seen from the curve $a$ of FIG. 4, as the velocity of the fluid in one direction increases, the output current substantially straightly increases to some value from the output current value when the fluid is stationary. Similarly, as the velocity of the fluid in opposite direction increases, the output current substantially straightly decreases to zero from the output current value when the fluid is stationary. The curves $b$ and $c$ show the output currents against the velocity of the fluid in respective cases wherein the applied voltages $V_{DS}$ across the drain D and the source S of the FET 300 are 15V and 10V, respectively. Thus, it will be noted that the currents flows from curves $a$ to $b$ and then to $c$ with the voltage $V_{DS}$, with the result that the direction and/or the velocity of the fluid flow to be detected vary so that a desired range of the velocity of the fluid flow to be detected is provided.

As Table I shows the measurement of various fluids by the detector 10 of FIG. 1 in combination with the external detecting circuit 50 of FIG. 3. In this measurement, the conduit 200 had the cross sectional area of 2.0 cm² and the net-like electrodes had the roughness of 150 meshes, as in the measurement of FIG. 4.

Table I

| $V_{DS}$(volt) | Velocity of the fluids (cm/sec.) | Deflection of the ampere meter (mA) | | | |
|---|---|---|---|---|---|
| | | nitrogen gas | liquefied nitrogen | insulation oil | Service water |
| 10 | 2 | 1.6 | 2.0 | 6.5 | 1.2 |
| | 10 | 7.0 | 9.0 | 6.6 | 2.4 |
| | 30 | 9.5 | 14.0 | 6.9 | 3.5 |
| 15 | 2 | 4.2 | — | 17.6 | — |
| | 10 | 14.4 | — | 17.8 | — |
| | 30 | — | — | 18.1 | — |

FIG. 5 shows another external detecting circuit which comprises an actuating circuit 53 associated with the detector 10 of FIG. 1 to actuate an indicator (not shown) for indicating the direction of the fluid flow. The actuating circuit 53 is shown to comprise a Schmitt trigger circuit 500 including NPN transistors 502 and 504 and an indicating signal output circuit 506 including a relay 508 controlled by the NPN transistor 510 of the Schmitt trigger circuit 500. The transistor 510 has the base connected to the output side of the Schmitt trigger circuit 500 or the collector of the transistor 504. The transistor 502 of the Schmitt trigger circuit 500 has the base connected through a lead 312 (not shown in FIG. 1) to the drain D of the FET 300, which drain is in turn grounded through a variable resistance 512 (also not shown in FIG. 1). Since the variation in the velocity of the fluid flow appears as variation in the current through the variable resistance 512 (corresponding to the curve $a$ of FIG. 4, for example), the voltage drop across the resistance 512 varies with the velocity of the fluid flow. Thus, the voltage drop across the resistance 512 increases or decreases relative to that when the fluid stops to flow. Between the emitter of the transistor 504 and the ground is connected a variable resistance 514 which serves to set the operating voltage of the Schmitt trigger circuit 500 and the value of which is so determined that the voltage across the variable resistance 514 is slightly higher than that across the resistance 512 when the fluid flow is stationary. Thus, with the voltage across the resistance 512 beyond that across the resistance 514, the Schmitt trigger circuit is operated to produce an output signal at the collector of the transistor 504. The transistor 510 of the output circuit 506 is then conductive so that the relay 508 is energized to close contactors 508$a$ and 508$b$ of the relay. The contactors 508$a$ and 508$b$ may be connected to an indicating circuit (not shown) so that it indicates the direction of the fluid flow through the detector 10 of the present invention. It will be understood that if the FET 300 is wired to the transducer 20 as shown in FIG. 3, then the indicator can indicate the presence of the fluid flow of the direction indicated by an arrow $a$ of FIG. 3.

FIG. 6 shows another external detecting circuit which comprises an actuating circuit 54 associated with the detector of the present invention and adapted to indicate whether the fluid flow in one direction stops or not. The actuating circuit 54 has a Schmitt trigger circit 500 identical to that of FIG. 5, the Schmitt trigger circuit including two NPN transistors 502 and 504. The same components are indicated by the same numerals as in FIG. 5. The relay 508 has the coil connected to the collector of the transistor 504, the emitter of which is connected to one end of the variable resistance 514 with the other end connected to ground. The variable resistance 512 is arranged between the drain D of the FET casing 252 may be mounted a copper plate electrode 256 opposite from the opening 250 in the conduit 248 in a similar manner. A central copper plate electrode 258 is securely mounted in the conduit 248 at the opening 250 in a fluid-tight manner so that the opening is closed by the electrode 258. In the electrode 258 at the center is carried a radiation source 260 in the suitable form exposed to both interiors of the conduit 248 and the casing 252. An ionizing area 262 to ionize the fluid is defined between the opposite electrodes 254 and 258 within the conduit 248. A closed ionizing chamber 264 is defined within the casing 252 to contain and ionize the fluid exposed to the electrodes 256 and 258. The electrodes 256 and 254 may be connected to the source S and the drain D of the FET 300 of FIG. 3, respectively and the electrode 258 to one of the gates $G_1$ of the FET 300. It is to be noted that the conductance between the electrodes 254 and 258 of the ionizing area 262 is also variable depending upon the concentration of ionizable component of the fluid in the ionizing area 262 or the pressure of the fluid therein. Accordingly, with the fluid having the same quality as that to be measured and the known concentration or pressure contained in the closed chamber 262, the concentration or pressure of the fluid to be measured can be detected by the transducer 26. A detector in which the transducer 26 of FIG. 10 has been used has shield means 42 similar to the shield means 40 of FIG. 1 as shown by dotted line in FIG. 10 and the FET not shown is disposed within the shield means 42. It will be understood that the transducer 26 of FIG. 10 can also detect the velocity of the flowing fluid therethrough. Moreover, it is to be noted that the transducer 26 can detect the velocity as well as the composition or pressure of the flowing fluid by use of the transducer 26 in combination with the transducer 20 of FIG. 3 in series connection to separate the value to be measured from the composite value of both the transducers 20 and 26. In addition, it should be understood that the transducer 26 can detect the flow rate of the fluid therethrough. In such case, it can be detected by comparing the amount per unit time of the fluid such as gas flowing at a given velocity through the ionizing area 262 with the reference amount of the fluid contained in the closed ionizing chamber 264. More specifically, the greater the amount of the fluid through the ionizing area is, the larger the number of ions in the fluid and on the other hand the less the amount of the flowing fluid, the less the number of ions in it, with the result that the conductance between the electrodes 254 and 258 varies depending upon the flow rate of the fluid through the ionizing area 262. Just as described in connection with the transducer 22 of FIG. 8, the transducer 26 is adapted to detect the fluid in the form of liquid having a higher density than gas because no obstacle is provided within the ionizing area 262.

A transducer 28 of FIG. 11 is substantially similar to that of FIG. 10 except that the electrode 258 of FIG. 10 partitioning the ionizing area 262 and the closed ionizing chamber 264 is replaced by a radiation non-permeative partition 266 of insulating material, at the bottom of which is provided a copper plate electrode 268 opposite to the electrode 254 and on the top of which is mounted a copper plate electrode 270 opposite to the electrode 256. On the electrode 268 is mounted a radiation source 272 by any suitable means to ionize the fluid within the ionizing area 262 and similarly on the electrode 270 is mounted a radiation source 274 by any suitable means to ionize the closed ionizing chamber 264. As seen from FIG. 11, the radiation source is axially offset from the middle point of the electrode 268 so that the transducer 28 can detect the direction of the fluid flow in addition to the composition or pressure as well as the velocity or flow rate of the fluid. The amplifier and the shield means have been omitted as in FIGS. 8 and 9.

Referring now to FIG. 12, there is illustrated a detector adapted to more stably detect the fluid through the transducer even when variation in ambient temperature occurs and which is substantially idential to the detector 10 of FIG. 1 except that the FET 300 is so arranged that it is exposed to the fluid flowing through the conduit 200. The same components have been indicated by the same numerals as in FIG. 1. The pipe block 202 is provided with an opening 276 which is closed by an insulating box 278 secured to the pipe block 202 by any suitable means. The FET 300 is securely mounted in the box 278 so that it contacts with the fluid through the pipe block in a thermally conductive relationship from the fluid. With the fluid of relatively lower temperature such as liquefied gas flowing through the transducer 29, it can detect the state of the fluid flow in a stabler manner even when ambient temperature varies because the FET can be stably operated at such lower temperature.

It will be understood by those skilled in the art that for soldering the leads of FIGS. 8 through 11 to the FET the transducers 22 through 28 preferably have electrically conductive layers (not shown) provided on the conduits or the conduits and the casing 252 at the outer surfaces thereof and connected to the respective electrodes by wires (not shown) embedded into the conduits or the conduits and the casing 252.

Although some preferred embodiments of the present invention have been described herein-above, they are by way of illustration of the present invention, but it is intended not to be limitted thereto. It will be understood that various modifications and changes in construction, arrangement and connection might be made without departing from the spirit and scope of the present invention, which has been defined only by the appended claims.

What is claimed is:

1. A flow meter for generally electrically non-conductive liquid, comprising a transducer to generate an electrical signal responsive to the flowing state of liquid therethrough, including a radiation source to ionize said liquid and first and second ionizing areas each having a pair of electrodes exposed to said ionized liquid and defining said respective ionizing areas, said first and second ionizing areas arranged in a flowing direction of said liquid; an amplifier having a high input impedance and a low output impedance and connected to said electrodes of said first and second ionizing areas; and electrically conductive shielding means to shield said transducer and said amplifier, characterized by that said transducer further includes a conduit by which said first and second ionizing areas are enclosed and into which said liquid is introduced so that it passes through one of said first and second ionizing areas and then through the other ionizing area, and that said amplifier together with its high impedance input side is disposed within the space between said conduit and said shielding means, with output lead means from said amplifier extending through and out of said shielding means for adaption to connection with an external circuit.

2. A flow meter as set forth in claim 1, wherein said pairs of electrodes are arranged spacedly in series in the axial direction of said conduit of said transducer, said electrodes each comprising a member through which said liquid permeates.

3. A flow meter as set forth in claim 2, wherein one of said pair of electrodes of said first ionizing area and one of said pair of electrodes of said second ionizing area comprise one common electrode.

4. A flow meter as set forth in claim 1, wherein said electrode pairs of said first and second ionizing areas each comprise flat plate electrodes spaced in a direction normal to said axis of said conduit.

5. A flow meter as set forth in claim 3, wherein said amplifier comprises a field effect transistor with the source and the drain of said transistor connected to said outside electrodes of said ionizing areas and with one of the gates of said transistor connected to said common electrode of said ionizing areas.

6. A flow meter as set forth in claim 4, wherein said amplifier comprises a field effect transistor with the source and the drain of said transistor connected to two electrodes on one side of said first and second ionizing areas and with one of the gates of said transistor connected to two electrodes on the other side of said first and second ionizing areas.

7. A flow meter as set forth in claim 1, wherein said shield means comprises a metal cylindrical body.

8. A flow meter as set forth in claim 1, wherein said amplifier includes a bridge connection, said pair of electrodes of at least one of said ionizing areas comprising one of the arms of said bridge connection, the output side of which is connected to the input of said amplifier.

9. A flow meter as set forth in claim 1, said flow meter measuring the flow state of low temperature liquid and wherein said amplifier is disposed in a thermal conducting relation to said liquid so that it never interferes with the flow of said liquid.

* * * * *